United States Patent [19]

Roper

[11] Patent Number: 4,753,893

[45] Date of Patent: Jun. 28, 1988

[54] METHOD AND ARTICLE FOR DETECTION OF IMMUNE COMPLEXES

[75] Inventor: Michael D. Roper, Lafayette, Colo.

[73] Assignee: Biostar Medical Products, Inc., Boulder, Colo.

[21] Appl. No.: 927,609

[22] Filed: Nov. 6, 1986

Related U.S. Application Data

[63] Continuation-in-part of Ser. No. 740,018, May 31, 1985, abandoned, and a continuation-in-part of Ser. No. 763,955, Aug. 8, 1985.

[51] Int. Cl.$^4$ .............................................. G01N 33/564
[52] U.S. Cl. ..................................... 436/509; 436/518; 436/531; 436/807; 436/810; 436/811
[58] Field of Search .............................. 436/506–509, 436/518, 531, 810, 811

[56] References Cited

U.S. PATENT DOCUMENTS

| | | | |
|---|---|---|---|
| 4,233,286 | 11/1980 | Soothill et al. | 436/507 |
| 4,307,190 | 12/1981 | Masson et al. | 436/821 |
| 4,329,331 | 5/1982 | Kallick | 436/506 |
| 4,332,783 | 6/1982 | Pernice et al. | 436/506 |
| 4,548,909 | 10/1985 | Parratt | 436/507 |

OTHER PUBLICATIONS

Jones et al, J. Immunol. Meth., 44(1981) 249–270.

*Primary Examiner*—Christine M. Nucker
*Attorney, Agent, or Firm*—Shoemaker & Mattare, Ltd.

[57] ABSTRACT

The use of the ability of immunologically non-specific peptide linked amino acid containing compounds to combine with anti-antibodies or rheumatoid factor to provide for a method of detecting rheumatoid factor and for a method of immobilizing circulating immune complexes from fluids for the purpose of detection or removal thereof from body fluids, such as serum or blood.

7 Claims, 11 Drawing Sheets

METHOD AND ARTICLE FOR DETECTION OF IMMUNE COMPLEXES

This application is a continuation-in-part of application Ser. No. 740,018 filed May 31, 1985 abandoned and a continuation-in-part of application Ser. No. 763,955 filed Aug. 8, 1985

BACKGROUND OF THE INVENTION

The immune system is the body's major defense mechanism against infections and neoplasm. The vertebrate immune system is divided into two functional parts; humoral immunity and cell-mediated immunity. Humoral immunity represents biomolecular components of the immune system which are produced by cells and secreted into the body's circulatory system. Cell-mediated immunity is characterized by the direct action of various leukocytic cells upon targeted foreign substances that are present in the body. Concerted action of these interrelated systems affords protection from a wide variety of infectious diseases and neoplasms.

Under normal circumstances, the presence of foreign substances in the body provokes a response from the cells which synthesize and secrete components of the humoral system. Specifically, B lymphocytes synthesize specific proteins, that is antibodies, which bind to selected sites on the foreign organism. After the antibodies bind to sites on the foreign organism or transformed cells, the foreign cells or viruses may then be destroyed through action of the cell-mediated immune system, or by the action of other humoral fractions, or directly inactivated by the antibody molecules themselves.

Ordinarily, antibody molecules are not directed at the host's own or "self" agents. In certain individuals, however, the immune system mistakenly mounts an immune attack against itself, much in the same manner that it would for a foreign invader. Inflammation, damage, or outright tissue destruction often results from these autoimmune responses. The results of such autoimmune conflicts are dramatic. Symptoms therefore diseases include the inability to utilize sugar (type I diabetes), destruction of joints (rheumatoid arthritis), kidney destruction (systemic lupus erythematosus, glomerulonephritis, and like diseases), and destruction of the vascular system (vasculitis). Each autoimmune disorder leads to prolonged suffering together with early mortality.

Many autoimmune diseases are accompanied by persistently high concentrations of blood-borne autoimmune complexes. These autoimmune complexes usually contain a variety of anti-antibodies, rheumatoid factors, and other species which form extended immune complexes together with the target antigens. Much of the damage produced by the autoimmune diseases may be traced to the efforts of the cell-mediated immune system to eliminate such extended autoimmune complexes, wherever they may be found. Control of these diseases has proven difficult in the past, partly because the detection methods employed inadequately discriminated between levels of extended immune complexes of normal and disease states.

Many different techniques have been attempted for obtaining accurate, rapid and inexpensive methods of immune complex detection. Many techniques are quite ingenious, but no method has proven to be totally adequate. Examples of the limitations in prior methods of detection follow.

Firstly, the Raji cell assay depends upon the presence of cell surface receptors for immune complexes, and these receptors only appear at precise times in the growth of the culture.

Secondly, complement fractions or monoclonal antibodies directed against them are often employed in radioimmuno- or enzyme-linked immunosorbent assays. Unfortunately, both complement and selected monoclonal antibody used to immobilize complement have been shown to be labile proteins. This instability, particularly in the complement fraction, leads to impaired test sensitivity, specificity and reproducibility. Consequently, methods which depend upon complement immobilization either by direct or antibody-mediated adherence, are inadequate for clinical testing because of this labile property of the complement and selected antibody.

Thirdly, immunoglobulin class and size limit the utility of complement-based assays. Neither Raji cell nor complement-based assays can detect all antibody classes and subclasses in the immune complex. These assays are restricted to IgM, $IgG_1$, $IgG_2$. Furthermore, they are restricted to complexes with molecular mass greater than 1,000,000 Daltons. These two criteria represent serious limitations because many harmful complexes are significantly smaller than 1,000,000 Daltons.

Lastly, liquid physicochemical techniques utilizing precipitation with substances like polyethylene glycol, dextran, or *Staphylococcus aureas* protein A are considered unwidely because of the difficulties inherent in handling small and often flocculent precipitates. Adventitious binding of immunologically unrelated immunoglobulins to the precipitate further degrades the performance of such tests. Together, these difficulties seriously impair the utility of physicochemical methods of immune complex measurement.

To overcome such limitations, numerous tests must be run, thereby increasing the cost to the patient. As a consequence, the various tests are not normally performed with sufficient frequency to monitor the progress of a patient's disease properly. Development of an inexpensive, selective, effective means of adhering the immune complex to a solid support is essential to overcome these problems.

It is therefore an objective of the present invention to provide compositions, methods and articles for the selective adsorption or affixing of immune complexes which will be effective for detecting a wide variety of classes and subclasses of immune complexes.

It is a further objective of this invention to overcome the aforementioned selectivity, stability, and handling disadvantages inherent in other methods of immune complex adsorption to solid surfaces for the purposes of assay, removal of immune complexes from serum, and the like.

It is yet a further objective of this invention to provide novel, highly adaptable, and readily utilizable means for the detection of components of said complexes after affixation to a support, and further to use such techniques for the purposes of clinical detection, removal, concentration, or any other purpose or utility associated with human or veterinary medical applications.

BRIEF SUMMARY OF THE INVENTION

The present invention includes novel compositions, novel methods and articles for the direct selective absorption, adsorption or attachment, by whatever mechanism, of immune complexes from serum or other body fluids either containing or devoid or rheumatoid factors and anti-antibodies, for the purpose of identification, quantitation or removal. The present invention utilizes, in its broadest sense, immunologically non-specific peptide linked amino acids, which have a particular affinity for attaching immune complexes, and more specifically to composites formed from combinations of immunologically non-specific peptide linked amino acids and anti-antibodies or rheumatoid factor, which have particular affinity for attaching, binding or otherwise immobilizing immune complexes. As described herein, the immunologically non-specific peptide linked amino acids and similar modified peptide linked amino acids alone or in the combinations described are employed to directly and selectively affix immune complexes from serum or other body fluids.

The immunologically non-specific peptide linked amino acids which can be employed advantageously in the practice of the present invention include oligopeptides, polypeptides, and proteins as well as modified or substituted oligopeptides, polypeptides and proteins. Preferably, polypeptides and proteins that are glycosylated or modified with functionally equivalent substitutes, such as thiosugars, hydroxy or thioamino acids, hydroxy or thiolipids, or chemically related or functionally similar substances, have been found to be capable of directly bonding with immune complexes, or bonding when formed in a composite layer together with anti-antibodies of rheumatoid factor. More preferably, glycosylated proteins are utilized (hereinafter glycoproteins) and most preferably, certain selected globulin fractions such as immunologically non-specific gammaglobulins are particularly effective in the practice of the present invention.

Whether the immune complexes comprise any single class or subclass of antibody or whether the fluid containing the immune complexes derives from corporeal or extracorporeal origin, does not limit the utility of the present invention, as physicochemical alterations to the antibodies, after binding to antigens render them selectively susceptible to immobilization.

The source of the glycoproteins selected for use herein is a particular purified gammaglobulin fraction (Cohn, E. J. (1946), *J. Chemical Society* 68, 459). These glycoproteins were derived from animals not immunized against human serum proteins or immune complexes derived therefrom. The "Fab" portion of these glycoproteins thus does not react with the "Fc" portion of antibodies comprising the immune complex in solution, regardless of whether those immune complexes contain anti-antibodies or other species. Instead, based on observations, they appear to affix complexes through interaction of the most highly glycosylated portion of the immobilized glycoprotein.

Such glycoprotein preparations have long been used to prevent adventitious adherence of free antibodies to solid supports. Nonetheless, it is unique and highly surprising to find that a coating of glycoproteins on a solid support can be used as further described herein to selectively affix extended immune complexes. Immune complexes will thus be adsorbed to a coating of gammaglobulins while free antibodies will not. The present invention now provides a way to substantially improve detection methods for simple and extended immune complexes such as in serum, in plasma, in the blood, and in other body fluids. It also provides a particularly useful method for selective removal of such complexes from the blood of those suffering from autoimmune and other diseases characterized by the formation of immune complexes.

According to the preferred practice of this invention, a simple or composite film of glycoproteins, selected from the group described herein, is first affixed to a solid support medium to serve as a selective adsorbent for affixing any immune complex as might be present in the fluid to be contracted with the film. The glycoprotein coat may be any possessing the described ability to affix the immune complex, an immunologically non-specific bovine gammaglobulin fraction obtained as described, being preferred.

In addition to the gammaglobulin fraction, the addition of anti-antibodies or rheumatoid factor separately or conjunctively with the material being applied as the coating provides for additional binding capacity for circulating immune complexes.

After applying the described coating to the solid support medium, the glycoprotein coated support can then selectively adsorb many species of immune complexes from a fluid containing immune complexes which is contacted with the coating. The affixed immune complexes may then be either: (1) assayed for any of their components, with any immunoassay method, the enzyme-linked immunosorption assay method being preferred; or (2) concentrated and purified; or (3) the fluid may be returned to the patient devoid of immune complexes, if desired, for a clinical therapeutic utility. In addition, the ability of the coating to adsorb immune complexes can be expanded greatly by cosorbing a second molecule (such as anti-antibodies, rheumatoid factor, or the like) to form a composite layer.

In the following examples the described film is formed by exposing the selected gammaglobulin fraction to pH-dependent denaturation; however, any form of fixation of the selected glycoprotein is suitable so long as the ability of the film to specifically and selectively affix immune complexes is retained. Such examples of fixation include, but are not limited to, thermal aggregation, chaotropic unfolding, crosslinking with chemical agents such as glutaraldehyde, drying, freezing, and the like methods.

Further, the dilution of the material being assayed with a glycoprotein will further enhance the selectivity of the system for immune complexes.

Subsequent qualitative or quantitative detection of the complex is thereby greatly simplified since enzyme-conjugated antibodies specific for any immunoglobin class are readily available. Final visualization or colorimetry of immune complexes is accomplished by ELISA techniques (Engvall and Perlman (1971) *Immunochemistry* 8, 871–874 and (1972) *J. Immunology* 109, 129, 235) and *The Enzyme Linked Immunosorbent Assay* (ELISA) by Voller, A., Bidwell, D. E. and Bartlett, A., (1979) Dynatech Laboratories, Inc., Alexandria, Va., both of which are, in their totality, incorporated herein by reference). It is also possible to detect specific antigens present in the complex using labelled probles which specifically bind that antigen. The addition of other glycoproteins such as rheumatoid factor allows for a broader specificity of binding of various types of CIC, and rheumatoid factor can be detected by its affixation to the glycoprotein coating and then utilizing tagged IgG which will only bond to the rheumatoid factor.

DETAILED DESCRIPTION OF THE INVENTION

Figure 1:
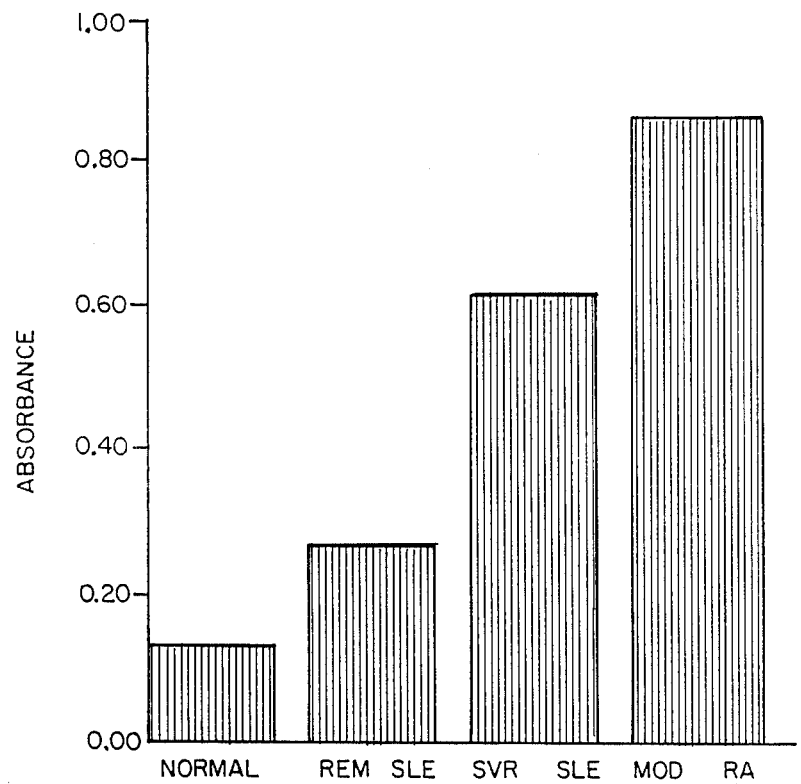
FIG. 1 is a bar graph of absorbance values for specific immunoassay of normal and disease states run according to the present invention.

The following definitions are supplied for the purposes of clarifying aspects of this invention:

Immunologically non-specific peptide linked amino acids: As used herein, this means a solution or coating used as described herein which contains oligopeptides, polypeptides and proteins as well as modified oligopeptides, polypeptides and proteins, which are derived from organisms which have not been immunizeed against any antigenic determinant derived from any part of the animal specie being tested or otherwise associated with such specie, or immune complexes derived therefrom and have the functional ability to attach to, adhere, affix, or otherwise immobilize in situ, simple or extended immune complexes present in such specie. In addition to the foregoing naturally occurring substances, this definition also includes peptide-linked amino acids which are created synthetically. Such synthesis can be accomplished in a peptide synthesizer or through similar chemical processes, or produced by genetic alteration of existing or newly created viruses, bacteria, fungi, existing or newly created viruses, bacteria, fungi, yeast or other recombinant, or hybrid cell vectors or hosts. It is therefore contemplated that the defined oligopeptides, polypeptides and proteins, and modified oligopeptides, polypeptides and proteins, derived from one specie that has not been actively immunized against another specie, or synthesized as described should be useful in the practice of the present invention if in combination they exhibit the ability to attach to, adhere, affix or otherwise immobilize, in situ, immune complexes present in the tested specie.

Glycoprotein: As used herein, is intended to mean any combination of polysaccharide and protein or polypeptide from an immunologically naive or immunologically non-specific peptide linked amino acid for which the two agents are attached through covalent bonds between the polysaccharide and protein/polypeptide.

Gammaglobulin: Any member of globular glycoproteins having electrophoretic mobility in the "gamma" region of serum proteins subjected to the procedure.

Immunoglobulin: Any member of the gammaglobulin fraction processing chemical ability to bind to another agent, such agents including proteins, carbohydrates, nucleic acids, complex lipids, simple organic compounds, or any other compound interacting with the immunoglobulin through topographically determined binding to the "Fab" region.

Antibody: A member of the Immunoglobulin class of proteins. Mammalian antibody molecules comprise at least two "Fab" and one "Fc" region in their structures.

Anti-Antibody: An antibody which binds to another antibody. Used herein, such species shall denote antibodies which react with antibodies after immune complexes are formed. Anti-antibodies shall further denote such antibodies as may bind to any class or subclass of antibody which forms an immune complex with the appropriate antigen.

Antigen: Any compound against which antibody molecules may be directed provided binding occurs to the antibody at the binding site found in the "Fab" portion of the antibody molecule.

Immunoglobulin Classes: Immune globulins separated according to electrophoretic mobility. Recognized classes of immunoglobulins include but are not limited to immunoglobulins A, D, E, G, and M. These classes are abbreviated IgA, IgD, Ige, IgG, and IgM respectively.

Immune complex: As used herein the term immune complex includes both simple and extended immune complexes. Simple immune complexes include the reaction products formed whenever antibodies combine with antigens without further binding of micromolecules. Extended complexes are formed whenever simple immune complexes additionally bind anti-antibodies, certain anti-ideotypic antibodies, rheumatoid factors, or other micromolecules not involved in initial immunization such as complement or oponins.

Immune Response: Any response of a particular immune system during which specific antigens act to cause the formation of antibodies directed against the antigen or to cause the specific activation of cellular defense mechanisms resulting in antigen engulfment, cytotoxic response, or other action by cells of the cell-mediated system.

Immunologically Naive: The condition of the immune system in an animal or group of animals, including human beings, which have never been actively exposed to a specific antigen in such a manner as to produce a product of an immune response, either humoral or cell mediated.

Immunologically non-specific: For the purposes of this patent application, the term "immunologically non-specific" shall mean antibodies or related proteins whose "Fab" regions are not directed at or selective for a given antigen through active exposure or immunization by a foreign protein or other foreign molecule.

Non-specific: Immunologically non-specific (see above).

Complement: A thermolabile substance normally present in serum, that is destructure to certain bacteria and other cells sensitized by a specific complement-fixing antibody.

Rheumatoid factor: An anti-antibody composed of any or all classes of immunoglobulin, IgG, IgM, IgA, IgD, or IgE which selectively binds to immunochemically altered regions of the "Fc" portion of immunoglobulin G. Such molecules are most generally formed as a component of immune complexes.

Rheumatoid factor complexes: Complexes of rheumatoid factor and immunochemically altered immunoglobulin G, the latter either being denatured or bound to additional antigens so as to form a second immune complex.

Serum: Is intended to mean the fluidic component of any bodily fluid remaining after cells and coagulable proteins such as fibrin which may be present in such bodily fluidic components have been removed by appropriate physical, chemical, or physicochemical means. Typically, this term refers to the residual watery fluid remaining after clotting of blood and removal of the clot, but in its broad sense is intended to include the fluidic component or cerebrospinal fluid, urine, interstitial fluid, cellular cytoplasm, and the like.

Alkaline carbonate buffer: Unless otherwise specified it is intended to mean a solution prepared to be the equivalent of one-tenth mole of sodium bicarbonate dissolved in 900 ml of demineralized water. The pH was adjusted to 9.6 with sodium hydroxide, and the volume of the solution was adjusted to one liter by the addition of demineralized water.

Bovine gammaglobulin solution: Purified bovine gammaglobulins (Cohn, E. J. (1946) J. American Chemical Soc. 68, 459) were dissolved in alkaline carbonate buffer at the extent of 1.0 mg bovine gammaglobulins/ml of solution.

Phosphate buffered saline: Sodium chloride was added to water to the final concentration of 9 g/l. To this solution was added 0.01 moles of potassium phosphate (monobasic). The pH was adjusted to 7.4 and the solution volume brought to exactly 1.00 liter by the addition of demineralized water.

Tween-20®: An Atlas Chemical Company trademark for a presently available polyoxyethylene sorbitan monolaureate. In the prior description, this compound was added to phosphate buffered saline for some steps. When indicated, Tween-20® was used at a concentration of 0.05% (v/v). Non-ionic detergents such as Tween-20® are used to prohibit adventitious binding of proteins. Of course, other surfactants can be use, if functional.

Conjugated antibodies: For the enzyme immunoassay portion of the determination, antibodies directed against human immunoglobulin fractions were obtained. These antibodies had been chemically conjugated with horseradish peroxidase to serve as a detection agent. Said antibody preparations were diluted between 500 and 2000 fold, in phosphate-buffered saline containing Tween® prior to use.

Substrate solution: To quantitate the horseradish peroxidase, a solution of orthophenylene diamine (400 ug/ml) was prepared together with 10 uM hydrogen peroxide in phosphate buffered saline. The solution was prepared just before use, and stored in the dark to prevent photolytic decomposition.

Labelled Antibodies: Any antibody substance which has been covalently or otherwise combined with a molecule or ion for the purpose of selectively identifying that group of antibodies. Such adduct molecules or ions include enzymes, fluorescent substances, radionuclides, and the like.

Labelled Antigens: Any antigen substance which has been covalently or otherwise combined with a molecule or ion for the purpose of selectively identifying that group of antigens. Such adduct molecules or ions include enzymes, fluorescent substances, radionuclides, and the like.

Optical Density (OD) or Absorbance: A number which refers to the color absorbance of a sample. Optical density is related to the percent of light transmitted through the sample by the following formula:

$$OD = 2 - \log (\text{percent transmittance})$$

Proteins and polypeptides, including glycoproteins and glycopeptides and the combinations described herein, can be affixed to plastics or other solid supports including polymers, resins, glass, and the like by denaturation at a predetermined pH, or by covalent coupling, or by other physical or chemical methods such as thermal aggregation, ultraviolet mediated crosslinkage with or without chemical crosslinking agents, or by other chemical or physical means or any combination thereof. In addition, solid supports may consist of the glycoproteins or glycopolypeptides, or like proteinaceous materials including composite materials either chemically or physically or both chemically and physically modified and then either spum into insoluble proteinaceous fibers with or without additional support and constitutive materials such as polymeric, resin, siliceous, or mineral fibers, or used after treatments other than spinning which result in a solid-phase material containing the desired glycoprotein, glycopolypeptide, or other like material. As described hereinafter, such glycoproteinaceous films or insoluble preparations possess the unusual and unexpected characteristics of selectively adhering simple or extended immune complexes which may be present in a sample of fluids, including but not limited to fluids of biological origin that are placed in contact with the film-coated solid support or are placed in contact with glycoproteinaceous preparations. Other naturally occurring glycoproteins such as rheumatoid factor can be used, as herein described, in combination with bovine gammaglobulins to broaden the specificity of the method for CIC detection.

What follows is a description of a preferred embodiment of the coatings of the present invention, together with the preferred methods for adhering immune complexes, such as may be found in a sample of bodily fluid, including a description of the method for detecting the complexes so bound to the solid support. Gammaglobulins obtained from an animal population not previously challenged with human serum proteins are preferred embodiments of this method. Broadly, improved immune complex specificity using adjunctive composite coats of glycolated polypeptides and glycoproteins such as anti-antibodies, rheumatoid factor and the like are preferred embodiments of this invention.

Step 1: Affixation of the Glycoprotein Coat

Purified bovine gammaglobulins alone or in combination with other naturally occurring glycoproteins are contacted with a buffer comprising 0.1 molar sodium bicarbonate, pH 9.6. The final concentration of gammaglobulins in the resultant solution is 1.0 mg/ml (w/v). This solution is used for preparation of the glycoprotein coat.

Figure 11:
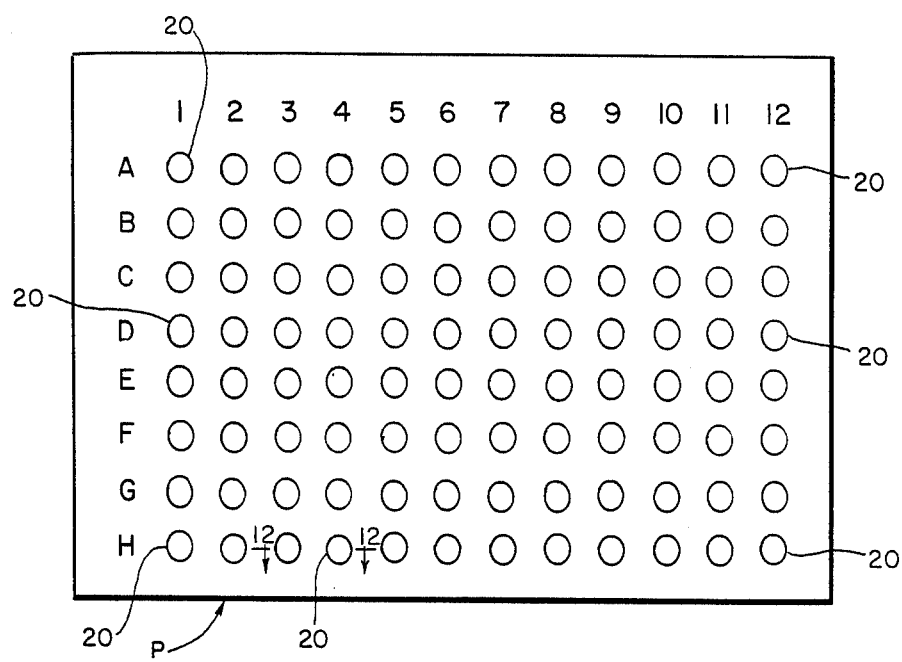
FIG. 11 is a top plan view of a microtiter plate which is adapted to form the article of this invention and is particularly useful in the immunoassay thereof.
Figure 12:
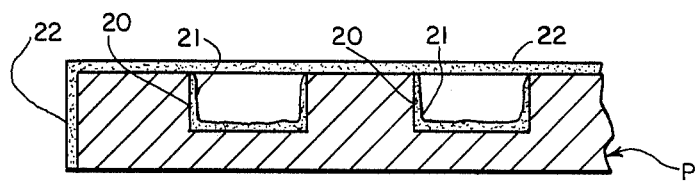
FIG. 12 is a fragmentary cross-section, taken along line 11—11 of FIG. 11 on an enlarged scale, showing the microtiter plate prepared for use.

To affix a thin film of bovine gammaglobulins to a receiving surface, 200 microliters of the previously prepared solution of bovine gammaglobulins is added to each well of a 96 well titer plate P, such as Dynatech Immulon II plate with a series of wells 20. As seen in FIGS. 11 and 12 the wells 20 of plate P are divided into both horizontal and vertical rows, with suitable indicia systems to indicate each specific well. In the system shown in FIG. 11, the wells of the vertical rows may be identified by numbers, as from 1 through 12, while the wells of the horizontal rows may be identified by letters, as from A through H, to provide an accurate correlation of the results with the samples being tested. As will be evident, there are 96 wells shown in the plate of FIG. 11, although the specific number of wells may be varied as desired. The plate is placed into a humidified chamber maintained at 37° C. and removed from the chamber after 4 hours. Although the embodiment described hereinafter is described for 96 well microtiter plates, the assay method works equally well in plastic tubes, including tubes molded with internal fins to increase the surface area. The coating time and bovine gammaglobulin concentration differ only slightly from those required for plate sensitization, and the results are comparable when the assay is performed in tubes, with or without fins, or in plates.

Unbound bovine gammaglobulin proteins or combinations therewith are removed by shaking the solution from the plate, then washing the plate thrice with a 0.9% (v/v) saline solution containing 0.01 molar potassium phosphate, pH 7.4, and leaving a thin coating 21 (FIG. 12) of bound gammaglobulin proteins. Optionally, a secondary fixative agent, such as anti-antibodies, rheumatoid factors, or like substances, may be added in conjunction with bovine gammaglobulins. Such adjunctive substances then form a composite layer of glycosylated polypeptides or glycoproteins copolymerized with the primary bovine gammaglobulin coating. The composite coat can be formed by the sequential or joint addition of the preferred gammaglobulin proteins and anti-antibody or rheumatoid factor to form a composite layer which can optionally be used as it is or additionally treated, as described, prior to use. The single additions can be in any sequence and the joint use may even include the simultaneous addition of fluids to be assayed before fixation or fixation and the optional use of coupling chemistry additions.

The adjunctive effect of this procedure is illustrated in Example 11. Preferably but not necessarily, a protective layer or film 22 (FIG. 12) formed of a suitable polymeric material may be affixed over open wells as shown in FIG. 11.

Step 2: Adhering Immune Complexes to the Prepared Plate Prepared in Step 1

Prior to contacting the bodily fluid with the prepared plate, the fluid is diluted properly by adding aliquots of serum to phosphate buffered saline. Dilution is necessary to yield appropriate amounts of color during step 2 (the enzyme linked assay). For most of the following examples, the optimum preferred dilution for this assay is 1:15 (volume serum:volume diluent). Wide latitudes of dilution are practicable, depending upon the nature of the bodily fluid subjected to the assay and the assay detection techniques employed. Preparation of the fluid may also include adding immunologically non-specific peptide linked amino acids (as defined herein) to the fluid.

The diluted sample of bodily fluid is then placed in appropriate wells of the titer plate. Adherence of the immune complexes contained in the samples to the solid support was enhanced by incubation at 37° C. for 30 minutes.

Following incubation to achieve complex adherence, the samples are shaken from the wells together with such non-complexed antibodies that are present in the sample. This is done since there are many more free antibodies than there are antibodies bound in complexes and residual free antibodies could elevate background absorbance values. The plates are then washed three times with phosphate-buffered saline, as described in Step 1 above. To this buffered medium is also added 0.05% (v/v) Tween-20® to further reduce adventitious binding of the free antibodies.

Step 3: Assay for Immune Complex Affixed to the Plate

Standard enzyme-linked assay techniques, previously described, are used for the assay of immune complexes, although any suitable means of detection such as radioactive labeling, fluorescence, or the like can be employed. For the examples described hereinafter, anti-human IgG induced in goats was used to ascertain whether the complex contained human IgG. These antisera were linked to horseradish peroxidase, an enzyme which yields a colored product whenever one of its substrates is present together with hydrogen peroxide. The substrate should be chosen to be consistent for the enzymic activity added to the antibody. For the examples described hereinafter, the substrate was orthophenylene diamine. Horseradish peroxidase and $H_2O_2$ produces nitroaniline from orthophynylene. Nitroaniline is chestnut brown in an acid solution, thereby facilitating quantitation. Many other substrates exist for this enzyme, and for other enzymes as well. For instance, peroxidase catalyzes the oxidation of tetramethylbenzidine into an intense blue product, easily detected with the naked eye. Alkaline phosphatase catalyzes the removal of phosphate groups from a wide variety of substrates, including p-nitrophenyl phosphate. The product of the p-nitrophenyl phosphate reaction is p-nitrophenol, which is intensely yellow. Other substrates such as thymolphosphate yield different colors when subjected to phosphatase action. The description of this embodiment does not limit the assay to any single means of detection, either by direct linkage of enzymes such as horseradish peroxidase, alkaline phosphatase, beta galactosidase, or the like, or to chemical reactant means, rather the assay method will perform equally well regardless of the detection scheme chosen. Such detection schemes may be, but are not limited to, enzyme-linked immuno-assay methods, whereby the enzyme used to detect the presence of the complex may be attached either to an antibody or to an antigen or other component selective for the presence of the immune complex affixed to the coating. Fluorescent antibody methods whereby any fluorescent substance is attached to the antibody or antigen or other substance used to detect the presence of immune complexes as may be affixed by the coating. In addition, indirect means of detection are also equally valid for the detection of immune complexes by this assay procedure. Such indirect means include but are not limited to second antibody techniques, biotin-avidin or biotin-streptavidin or similar adjunctive amplification schemes, or any other indirect means of detection of the presence of immune complexes in the coating. Furthermore, the assay is equally valid if biological means to detect the presence of the immune complex is affixed to the coating. Such means include the use of live or killed cells obtained either from cell culture or from living or dead organisms, whether prokaryotic or eukaryotic, and without regard to colonial or solitary organization. Any component derived from such biological preparations, including but not limited to nucleic acids, nuclear components, cytoplasmic or membranous components, lectins, receptors, opsonins, or other naturally occurring materials may be used to detect the presence of immune complexes affixed to the coating, provided such lectins, receptors, opsonics, or other naturally occurring materials are capable of interacting with the immune complex or any component part thereof. Lastly, detection of immune complexes affixed to the coating by any means either chemical or physical is also equally applicable to the assay protocol as extended from the embodiment listed herein. Such means may include but are not limited to changes in solution pH, polarity of light, changes in refractive thicknesses, changes in electronic characteristics such as conduction or piezoelectric behavior or dielectric constants of capacitors, changes in the specific heat content of the surface, or any other physical means used to detect the presence of matter in close proximity to other matter.

The immune complex indicator system, prepared as described, is then added to each of the wells of the titer plate. The plate is incubated with antibodies to the human IgG fraction of the complex for 15 minutes at 37° C. The plate is removed from the incubating chamber, emptied of its contents, and washed as in Step 2. The last wash is performed with Tween ®-free buffer to avoid inhibition of the attachment of the horseradish peroxidase enzyme.

The amount of enzyme label, as previously described, is determined by incubating the plates in the dark with a substrate solution at room temperature. The solution also contains phosphate-buffered saline, ortho-phenylamine diamine (400 ug/ml) and 3–10 micromolar hydrogen peroxide. The substrates are permitted to react for 10 minutes, or until sufficient color appears to be read on the colorimetric device used. The reaction is subsequently stopped through the addition of an equal volume of 2.5 molar sulfuric acid, and the intensity of color (the optical density, or OD or absorbance) is read by a colorimetric device such as a Dynatech MR600 or the like.

As with any enzyme-linked immune assay, the resultant color of the reaction product is proportional to the number of conjugated antibodies which have bound to the immune complex. For most cases, the number of bound conjugated antibodies is linearly related to the number of human IgG molecules present in the immune complex. Hence, as the amount of immune complex fixed on the film increases, so does the optical density, or absorbance of the enzyme reaction.

EXAMPLES

Example 1

SELECTIVITY OF GLYCOPROTEIN FILMS FOR ABSORPTION OF IMMUNE COMPLEXES FROM SERUM

A polystyrene plate was coated with a film of bovine gammaglobulins by the following procedure:

1. Purified bovine gammaglobulins from a Cohn fraction II preparation were dissolved in an alkaline buffer (0.1M sodium carbonate, pH 9.6).
2. The alkaline solution containing the bovine gammaglobulins was placed in contact with the plate for 4 hours at 37° C.
3. The coating solution was shaken from the plate, after incubation. The plate was washed three times with a solution of phosphate buffered saline to remove unbound gammaglobulin proteins.

The bovine gammaglobulin-coated plate was then used to determine the presence of immune complexes in human serum samples drawn from individual with:

1. no apparent pathology; (NORMAL)
2. systemic lupus erythematosus in remission (REM SLE);
3. moderate systemic lupus erythematosus or advanced systemic lupus erythematosus, (SVR SLE); and
4. moderate rheumatoid arthritis (MOD RA).

These sera had been previously shown to contain immune complexes appropriate for their pathological status by Clq ELISA tests and radial immunodiffusion methods.

A representative immune complex assay, as described hereinafter, using the bovine gammaglobulin-coated plates, prepared as previously described, is presented in Table 1, and graphically displayed in FIG. 1. The procedures used to derive these data are summarized below:

1. Sera were diluted properly with a solution of phosphate buffered saline prior to the test (hereinafter denoted PBS). In this example, one volume of serum was diluted with 15 volumes of PBS.
2. 0.1 ml aliquots of the diluted sera were placed into appropriately designated wells. For this example, 7 replicate determinations were performed on each specimen, and averaged.
3. The plate containing the specimens was placed into a humidified incubator at 37° C. for 30 minutes. Following incubation, the plate was removed from the incubator, the liquid shaken out, and the plate washed three times with PBS containing 0.5 ml polyoxyethylene sorbitan monolaurate (Tween-20 ®) per liter of solution.
4. The plate was exposed to a mixture containing horseradish peroxidase conjugated antibodies specific for the gamma chain of human immunoglobulin G. The plates were incubated at 37° C. for 15 minutes to attach the conjugated anti-IgG. After incubation, the plates were washed thrice with PBS to remove the unbound enzyme-conjugated antibodies.
5. Each well in the plate was assayed for horseradish peroxidase activity by adding PBS containing o-phenylenediamine and hydrogen peroxide. The presence of complexes was thus detected by the intense chestnut-brown color appearing after reaction was terminated with sulfuric acid. The color was quantitated at 490 nm using a Dynatech MR 600 plate reading colorimetric. Reagent blanks for colorimetric calibration were wells in the plate which were not contacted with human serum.

TABLE 1
ADSORPTION OF IMMUNE COMPLEXES BY GLYCOPROTEIN COATS

| Serum Source | Mean Optical Density (Mean Adsorbance) | Standard Error |
| --- | --- | --- |
| Normal | 0.133 | 0.004 |
| Remission SLE | 0.269 | 0.006 |
| Severe SLE | 0.617 | 0.008 |
| Moderate RA | 0.869 | 0.013 |

Legend:

The numbers listed under "Mean Optical Density (Mean Absorbance)" refer to the optical density read at 490 nm, obtained during the assay described above.

The optical densities listed are the average of seven assays per sample.

The number under the Standard Error heading refers to the standard error of the mean.

Abbreviations:
SLE: Systemic Lupus Erythematosus
RA: Rheumatoid Arthritis

The ability of bovine gammaglobulin-treated support media to adsorb immune complexes is demonstrated by the increased absorbance exhibited in wells exposed to serum drawn from individuals diagnosed as suffering from immune complex disease. Furthermore, good correlation was observed between the severity of disease and the amount of color found by the procedure. Normal human serum did not elicit appreciable color in the assay. These results provide additional evidence of coated plate specificity for immune complexes. The same procedure has been demonstrated to work equally well for whole blood and anticoagulated plasma.

Example 2

ADSORPTION OF IMMUNE COMPLEXES FROM SERUM BY UNCOATED POLYSTYRENE PLATES

Figure 2:
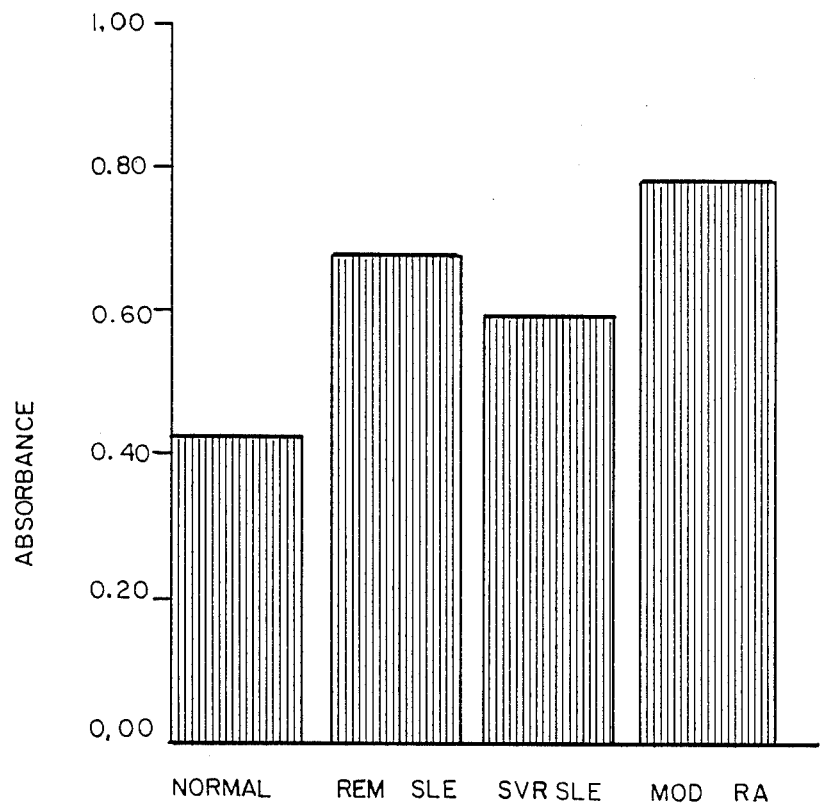
FIG. 2 if a bar graph of absorbance values for specific immunoassays of normal serum and serum containing immune complexes run on uncoated polystyrene plates.

To demonstrate the beneficial effect of glycoprotein coating, an uncoated polystyrene plate was exposed to the sera described in Example 1 under identical incubation conditions. The plate was then exposed to peroxide-conjugated anti-IgG and assayed for peroxidase as before. As expected, only slight selectivity is exhibited by untreated plates. Additionally, very high backgrounds were also observed, unlike the high selectivity and background found for plates precoated with glycoproteins such as bovine gammaglobulins. The results obtained by this procedure are presented in Table 2 and displayed graphically in FIG. 2. Each bar height shown in FIG. 2 represents the mean absorbance for seven replicate assays.

TABLE 2
ADSORPTION OF IMMUNE COMPLEXES BY UNCOATED POLYSTYRENE

| Serum Source | Mean Optical Density (Mean Adsorbance) | Standard Error |
| --- | --- | --- |
| Normal | 0.431 | 0.020 |
| Remission SLE | 0.682 | 0.021 |
| Severe SLE | 0.599 | 0.041 |
| Moderate RA | 0.781 | 0.031 |

Legend:

As in Table 1, the numbers listed under Optical Density refer to the numbers listed under "Mean Optical Density (Mean Absorbance)" refer to the optical density read at 490 nm, obtained during the assay described above.

The optical densities listed are the average of the results of seven assays per sample.

The number under the Standard Error heading refers to the standard error of the mean.

Colorimetric blanks were performed using uncoated plastic wells not exposed to human serum. Such blanks were treated to all subsequent steps including exposure to conjugated antibodies and assay for peroxidase. No color was apparent in the blank wells.

Abbreviations:
SLE: Systemic Lupus Erythematosus
RA: Rheumatoid Arthritis

Example 3

Figure 3:
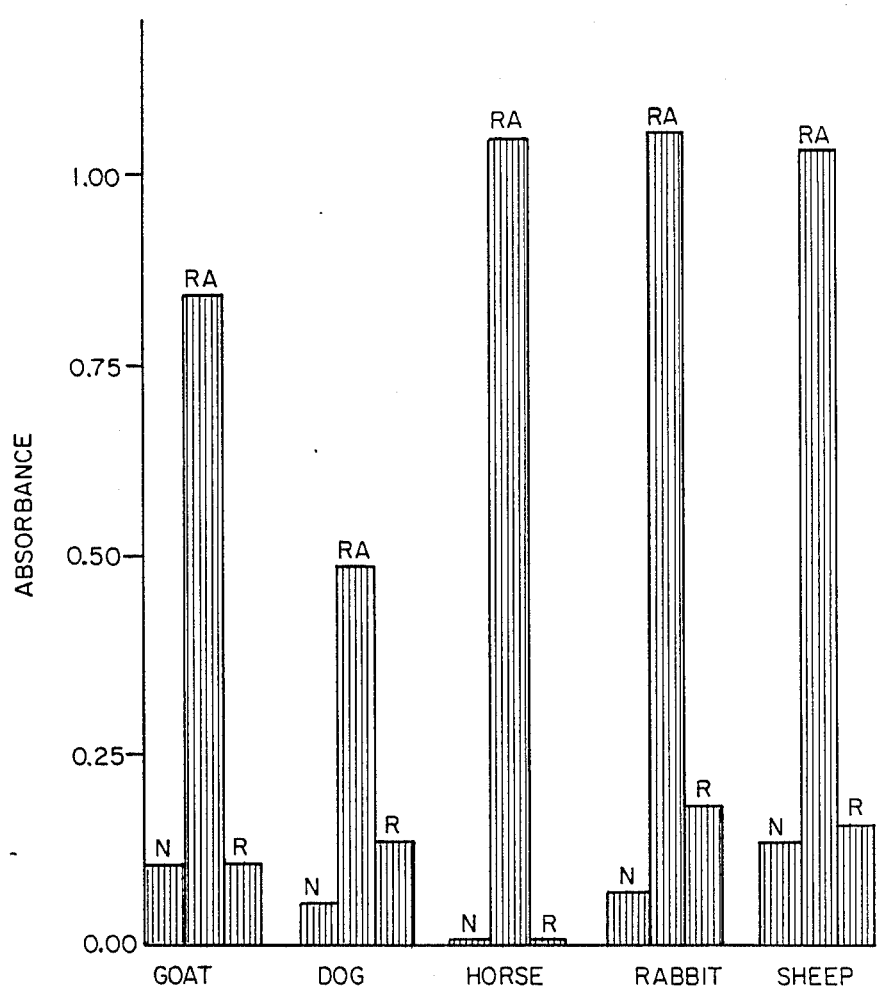
FIG. 3 is a bar graph of absorbance values for specific immunoassays using immunologically non-specific glycoproteins from the sources indicated.

Purified gammaglobulins from a variety of species were used for plate treatment as described in Example 1. The plates were subsequently exposed to immune complex rich or immune complex poor sera as described in Example 1. Following exposure and washing, the plates were assayed for present of attached immune complexes using horseradish peroxidase-conjugated anti-IgG as described in Example 1. The results of these treatments are presented in Table 3, and graphically displayed in FIG. 3.

TABLE 3
ADSORPTION OF IMMUNE COMPLEXES FROM SERUM BY POLYSTYRENE PLATES COATED WITH GAMMAGLOBULINS FROM VARIED SPECIES

| Coating Source | Normal | Rheumatoid Arthritis | Remission Lupus |
| --- | --- | --- | --- |
| Goat | 0.102 | 0.831 | 0.108 |
| Dog | 0.052 | 0.483 | 0.136 |
| Horse | 0.001 | 1.040 | 0.001 |
| Rabbit | 0.068 | 1.045 | 0.178 |
| Sheep | 0.131 | 1.024 | 0.154 |

Legend:

The numbers listed in TABLE 3 refer to the "Mean Optical Density" (Mean Adsorbance) at 490 nm obtained following the treatment listed above for plates coated with gammaglobulin fractions derived from the species listed on the left edge of the table.

Serum sources are listed along the top edge of the table.

Abbreviations:
SLE: Systemic Lupus Erythematosus
RA: Rheumatoid Arthritis

The fact that gammaglobulin mediates the ability of coated supports to specifically affix immune complexes is illustrated by comparison of Table 3 with Table 1. Each coating material affixed immune complexes from human sera appropriate with the pathology of the individual donor. Hence, all gammaglobulin coatings tried conferred selectively for immune complex absorption, although different qualities may be observed for different coatings. The same procedure works equally well for whole blood or anticoagulated plasma.

Example 4

REMOVAL OF IMMUNE COMPLEXES BY COATED POLYSTYRENE BEADS

Figure 4:
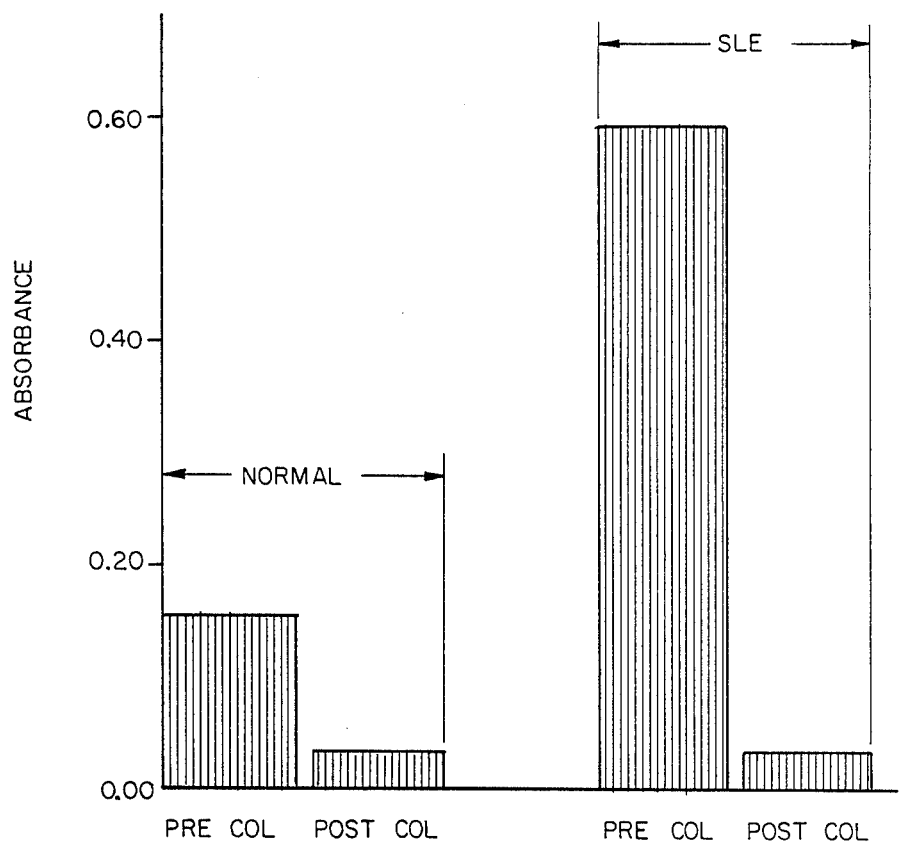
FIG. 4 is a bar graph of immunoassay results on sera before and after adsorption of the immune complexes in a column that has been pretreated with immunologically non-specific glycoproteins.

An alkaline preparation of bovine gammaglobulins (1 mg bovine gammaglobulins/ml in pH 9.6 carbonate buffer, as in Example 1) was used to coat polystyrene beads (BioBeads, SM4, 20–50 mesh, BioRad Laboratories, Richmond, Calif.) for the purpose of adhering immune complexes to the beads. Serum containing immune complex level as in Example 1, was passed through a column of said beads maintained at 37° C., and the quantity of immune complexes determined both before and after column filtration. The results of this procedure are presented in TABLE 4, and are displayed graphically in FIG. 4.

TABLE 4

REMOVAL OF IMMUNE COMPLEXES FROM SERUM BY COATED POLYSTYRENE BEADS

| Serum Source | Pre-Column OD | Post-Column OD |
| --- | --- | --- |
| Normal | 0.155 | 0.033 |
| Severe SLE | 0.601 | 0.035 |

Legend:
Serum samples from people with SLE and from healthy people were passed over separate columns treated with alkaline bovine gammaglobulins as previously described.

Immune complex assays were performed before and after treatment (pre- and post-column).

The optical densities exhibited by the samples before and after treatment are listed in the table.

Abbreviations:
SLE: Systemic Lupus Erythematosus

Polystyrene beads coated with bovine gammaglobulins in this manner selectively and expeditiously absorbed immune complexes. Approximately 90% of the complexes were removed by one passage through the column. Alkaline gammaglobulin treatment of polystyrene beads is thus effective in relatively quickly removing these agents from serum samples. Therefore, a sufficiently large column prepared with similar glycoproteins will remove significant amount os immune complexes when whole blood is passed through the column at through-put rates that can enable the present invention to be used in therapeutic treatment methods. Serum treatment in this manner will facilitate selective removal of simple and extended circulating immune complexes present. Furthermore, column isolation of immune complexes from large quantities of blood will provide for concentration of said complexes. This effect will allow for detection of minor components such as immunoglobulin idiotypes, rare subclasses of antibodies, and rare or sequestered antigens or anti-antibodies such as rheumatoid factors as might be present in said complexes. The same procedure will work equally well for anticoagulated plasma. cl Example 5

The purpose of this example is to illustrate the beneficial effect of the joint use of liquid-phase bovine gammaglobulin or immune complex assays performed on immobilized glycoprotein coats. This addition proves highly effective at reducing baseline values for this normal serum sample containing low levels of immune complexes. For this example, two serum samples were tested. The first of these samples donated by an individual exhibiting no apparent clinical pathology, but still reacting positive in the immune complex assay previously described. The second sample was obtained from an individual having a severe case of systemic lupus erythematosus. These two serum samples were diluted with phosphate buffered saline, or with phosphate buffered saline containing bovine gammaglobulin at a concentration of 1 mg bovine gammaglobulin per ml of buffer.

After diluting the samples, each of the four preparations was tested for immune complexes according to the solid-phase assay previously described particularly in Examples 1 through 3. The chestnut-brown color arising from the enzyme-linked portion of the assay was read at 490 nm on a Dynatech MR 600 plate reader. The results of this study are listed in the accompanying table and plotted on a bar graph.

TABLE 5

| Dilute Serum Source | BGG Absent Absorbance | BGG Present Absorbance |
| --- | --- | --- |
| Normal | 0.739 | 0.020 |
| SLE | 0.390 | 0.323 |

Legend:
Serum derived from clotted blood was used for the tests in the table above. The designation "Normal" is herein used to denote serum derived from an individual showing no clinically apparent manifestation of disease at the time of phlebotomy. The designation "SLE" is used in this example to denote serum derived from an individual clinically diagnosed as suffering from systemic lupus erythematosus. Prior to assay, 1 part serum was diluted with 15 parts of diluting agent. For the "BGG Absent" column, the diluting agent used in this example was phosphate buffered saline. For the "BGG Present" column, bovine gammaglobulin was dissolved in phosphate buffered saline to the extent of 1.0 mg bovine gammaglobulin per ml of phosphate buffered saline.

The diluted sera were subjected to the immune complex assay described in Examples 1 through 3. The numbers presented in the table represent the mean absorbance for four replicate determinations.

Figure 5:
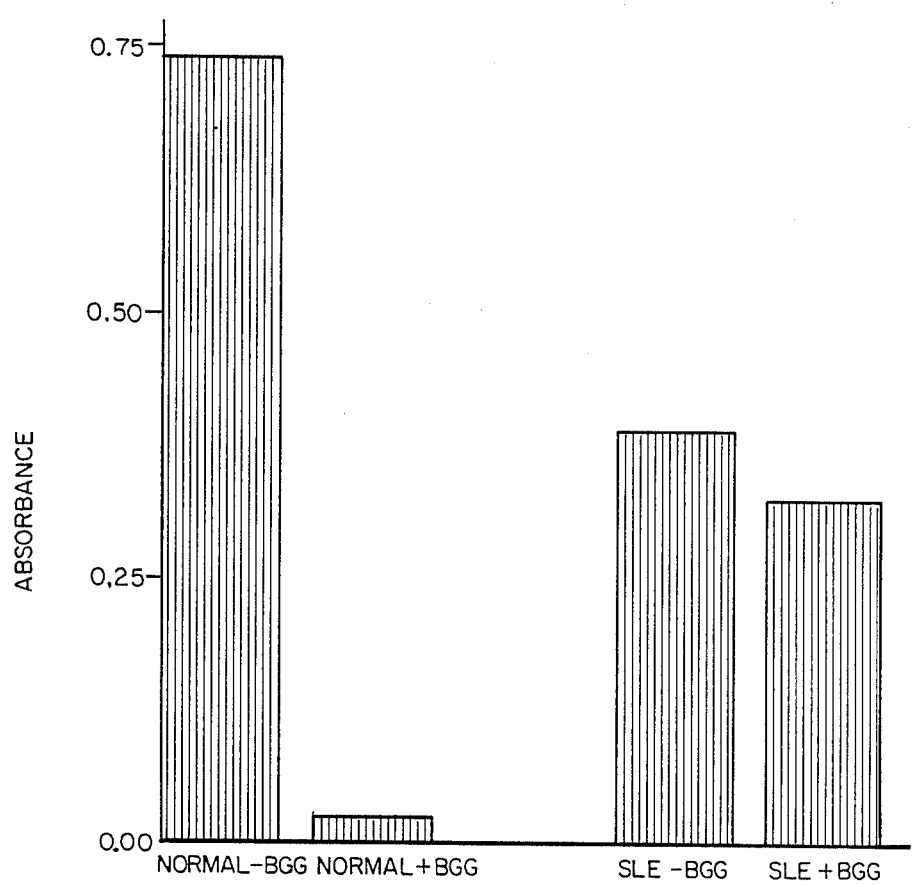
FIG. 5 is a bar graph of the results of another embodiment of the present invention.

In FIG. 5 the results of serum samples diluted either with phosphate buffered saline or with phosphate buffered saline containing 1 mg bovine gammaglobulin per ml are shown. After dilution, the samples were assayed for immune complexes using the solid-phase assay described in Examples 1, 2 and 3. The height of the bar in FIG. 5 represents the mean absorbance found after four replicate assays. In FIG. 5, normal refers to serum obtained from an individual presenting no apparent clinical pathology. SLE refers to serum obtained from an individual suffering from severe systemic lupus erythematosus. BGG Absent refers to serum diluted in phosphate buffered saline alone while BGG Present refers to serum diluted in phosphate buffered saline containing 1 mg bovine gammaglobulin per ml.

The addition of bovine gammaglobulin to the serum diluent reduced the absorbance found in the normal serum sample nearly forty-fold. Indeed, very little color was observed when the assay was performed on bovine gammaglobulin diluted normal serum. Conversely, the use of bovine gammaglobulin-containing diluent did not substantially reduce the absorbance when serum was obtained from someone with authentic autoimmune disease. Accordingly, a sixteen fold difference between normal and autoimmune state serum was noted after dilution by bovine gammaglobulin-containing buffer whereas no differentiation existed without such addition. In additional similar assay trials, this procedure essentially eliminates false positives for individuals without apparent pathology while not materially affecting rates of true positive indications. These results clearly indicate the beneficial effect of inclusion of glycoproteins like bovine gammaglobulin in the diluting agent, such effect being effective to eliminate the false positive rate without materially altering the true positive rate.

Example 6

The foregoing examples illustrate the utility of the immune complex affixation method described in this patent. The data presented in this example demonstrates that the fixation techniques described heretofore are also applicable to plasma and whole blood, regardless of which common anticoagulant is used.

For this example, blood was collected from a healthy donor and from an individual with rheumatoid arthritis. Four tubes were drawn from each donor. The first tube contained no anticoagulants. The three remaining tubes contained anticoagulants. The fine concentration of ethylene diamine tetraacetate (EDTA) in the second tube was 1.5 mg EDTA/ml blood; the final concentration of heparin in the third tube, 28 USP units heparin/ml blood; the final concentration of sodium citrate in the fourth tube, 3.5 mg sodium citrate/ml blood.

The specimens were prepared and assayed as follows:

The first pair of specimens (one each from normal and CIC elevated subjects) were allowed to clot normally, and the sera collected. These sera were assayed for immune complexes as described in Examples 1 and 5.

Aliquots of whole blood were removed from tubes 2-4 (anticoagulated with EDTA, heparin, and sodium citrate respectively). These aliquots were assayed as described in Examples 1 and 5. Plasma was separated centrifugally from the blood remaining in each tube and assayed as described in Examples 1 and 5.

Figure 6:
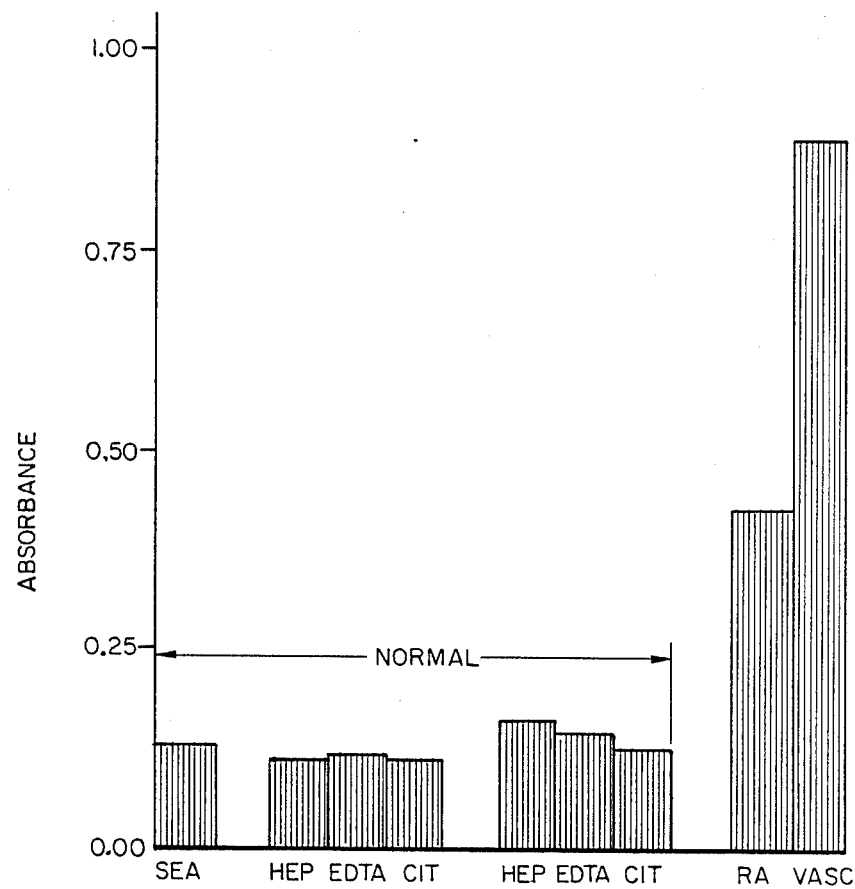
FIG. 6 is a bar graph of the results of using the present invention with whole blood.

The results of these investigations are listed in Table 6, and illustrated graphically in FIG. 6.

Referring to Table 6, it is clear that adding anticoagulants to whole blood does not alter assay discrimination for specimens containing normal and elevated amounts of immune complexes. In general, addition of anticoagulants improves assay performance slightly, as is evidenced by the higher fold elevation values observed for serum vs. plasma and whole blood samples. This finding fundamentally rules out mechanisms of immune complex adherence in which binding is mediated by complement or conglutinin or the like. Such agents require calcium ions for activity, and the addition of either EDTA or citrate removes free calcium from blood. As a consequence, it may be concluded that this example both illustrates the utility of the thin glycoprotein film method of immune complex affixation, and highlights the surprising properties of such thin glycoprotein films as used in the assay.

Assay values for serum samples from individuals exhibiting immune complex disorders are significantly elevated compared to these from normal individuals. This is found without regard to the presence or type of anticoagulant used. Accordingly, the procedure described for the affixation of immune complexes may be used with plasma or whole blood samples for the assay or for removal of such complexes as might be present in them according to the procedures described. It is apparent from the foregoing tests that there is no reason to believe that the method for removing immune complexes described herein is restricted to those found in serum, plasma, or blood. It is apparent that simple or extended immune complexes present in diverse sources such a urine, ascites fluid, or cerebrospinal fluid, capable of being affixed to the glycoprotein coating described herein, thereby greatly enhancing the utility of the invention described herein. Indeed, as is shown in Example 7, the principle of immune complex removal from anticoagulated whole blood and/or plasma by passage through a column prepared from glycoprotein-coated beads also applies to the therapeutic apheretic removal of immune complexes from patients afflicted with autoimmune disorders.

TABLE 6

IMMUNE COMPLEX ASSAY OF SPECIMENS DERIVED FROM WHOLE BLOOD

| Condition | Absorbance | Correction (Dilution Factor) | Final Absorbance | Fold Elevation |
|---|---|---|---|---|
| NORMAL | | | | |
| Serum | 0.128 | 1.00 | 0.128 | 1 |
| Plasma-hep | 0.107 | 1.00 | 0.107 | 1 |
| Plasma-EDTA | 0.118 | 1.00 | 0.118 | 1 |
| Plasma-cit | 0.099 | 1.11 | 0.110 | 1 |
| Whole blood-hep | 0.107 | 1.49 | 0.159 | 1 |
| Whole blood-EDTA | 0.095 | 1.49 | 0.142 | 1 |
| Whole blood-cit | 0.075 | 1.66 | 0.124 | 1 |
| CIC ELEVATED | | | | |
| RA plasma | 0.765 | 1.00 | 0.765 | 6 |
| plasma-hep | 0.864 | 1.00 | 0.864 | 8 |
| Plasma-EDTA | 1.031 | 1.00 | 1.031 | 9 |
| Plasma-cit | 0.830 | 1.11 | 0.921 | 8 |
| Whole blood-hep | 0.637 | 1.80 | 1.145 | 7 |
| Whole blood-EDTA | 0.733 | 1.80 | 1.318 | 9 |
| Whole blood-cit | 0.579 | 2.12 | 1.227 | 10 |

Legend:

Samples were obtained either from an individual free from clinically apparent pathology (Normal) or from individuals with rheumatoid arthritis (RA) or vasculitides. Serum refers to serous specimens obtained after centrifuging clotted blood. Plasma refers to the supernatant fluid obtained after centrifuging whole blood containing an anticoagulant. Anticoagulants are abbreviated as follows: (1) hep—heparin; (2) EDTA—ethylene diamine tetraacetate; and (3) cit—citrate. When noted in the table, anticoagulated whole blood was tested. Factors refer to volume corrections necessary because of added volume (citrate) or cell volume in whole blood. Citrate solutions comprise 10% of the final volume. Hematocrits were taken as 34% of blood volume for normals and 44% for CIC elevated samples. Fold elevation refers to the absorbance in any given CIC-elevated specimen divided by that found for its respective normal.

Four specimens of blood were withdrawn from each individual, one in a tube devoid of anticoagulants, and three separately containing different anticoagulants. The following abbreviations refer to the anticoagulant contained in specimens thus obtained: (1) hep—heparin, 28 IU/ml; (2) EDTA—ethylene diamine tetraacetate, 1.5 mg/ml; and (3) cit—sodium citrate, 3.5 mg/ml. Whole blood, plasma or serum (SER) derived from the specimen were subjected to the assay described fully in Examples 1 and 5. In the figure, the height of the bar represents the absorbance measured following the assay procedure. The data from this table is shown graphically in FIG. 6.

Example 7

As indicated in Example 4, columns prepared from glycoprotein coated solid supports exhibit the capacity of extracting immune complexes from serum samples. Further utility of such columns is afforded by the data presented in the present example. Samples of bodily fluids such as blood are often prohibited from clotting through the addition of anticoagulation agents such as heparin, ethylene diamine tetraacetate (EDTA) or salts of citric acid. Such compounds inhibit clotting either by interfering with the proteolytic steps leading to fibrin activation (heparin), or by chelating calcium (EDTA or citrate). In this example, it is shown that such agents as heparin, EDTA, or citrate are without effect upon the ability of glycoprotein coated solid supports to adsorb or affix immune complexes regardless whether the sample passed through the column was whole blood or plasma derived therefrom. Furthermore, immune complex fixation in the presence of these anticoagulants was at least as equal to that for serum, devoid of anticoagulants. The concentrations of anticoagulants tested for this example were higher than those normally used for apheretic purposes in human beings. Because these high concentrations of anticoagulants exhibited no deleterious effects on immune complex adsorption, it is obvious that the intermediate anticoagulant concentrations used for apheretic applications will similarly be without deleterious effects upon the immunoadsorption of complexes.

For the purpose of this example, blood specimens from an individual afflicted with rheumatoid arthritis were drawn into tubes containing either heparin, EDTA, or sodium citrate. A control speicmen was also drawn into a tube containing no anticoagulant. The control specimen was allowed to clot and the serum reserved. Immune complex assays were performed as described in Example 1, except that the incubation for immune complex detection (second incubation) was performed with horseradish peroxidase-conjugated goat antiserum directed against immune classes IgG, −M and −A were used in place of the IgG specific antibodies used in Example 1. Use of such multivalent antibodies as these (IgG, −M and −A specific) further enhances the chemical sensitivity of the test, thereby improving the general applicability of the adsorption method presented herein.

Following the immune complex assay, 0.25 ml aliquots of undiluted samples were added to columns prepared from BGG coated polystyrene beads as described for Example 4. The columns were incubated at 37° C. for 30 minutes, as before. The sample was then eluted as a bolus without appreciably dilution. Additional phosphate buffered saline was passed through the column to remove loosely bound immune complexes from the column. The resulting diluted eluate was subsequently assayed for immune complexes without additional dilution. An additional control was also prepared in which serum was incubated in contact with untreated polystyrene beads. The eluate of that column was also assayed as above.

The percent of immune complexes removed by the procedure was calculated as follows:

$$\% \text{ Removal} = \frac{OD_{init} - OD_{final}}{OD_{init}} \times 100$$

Figure 7:
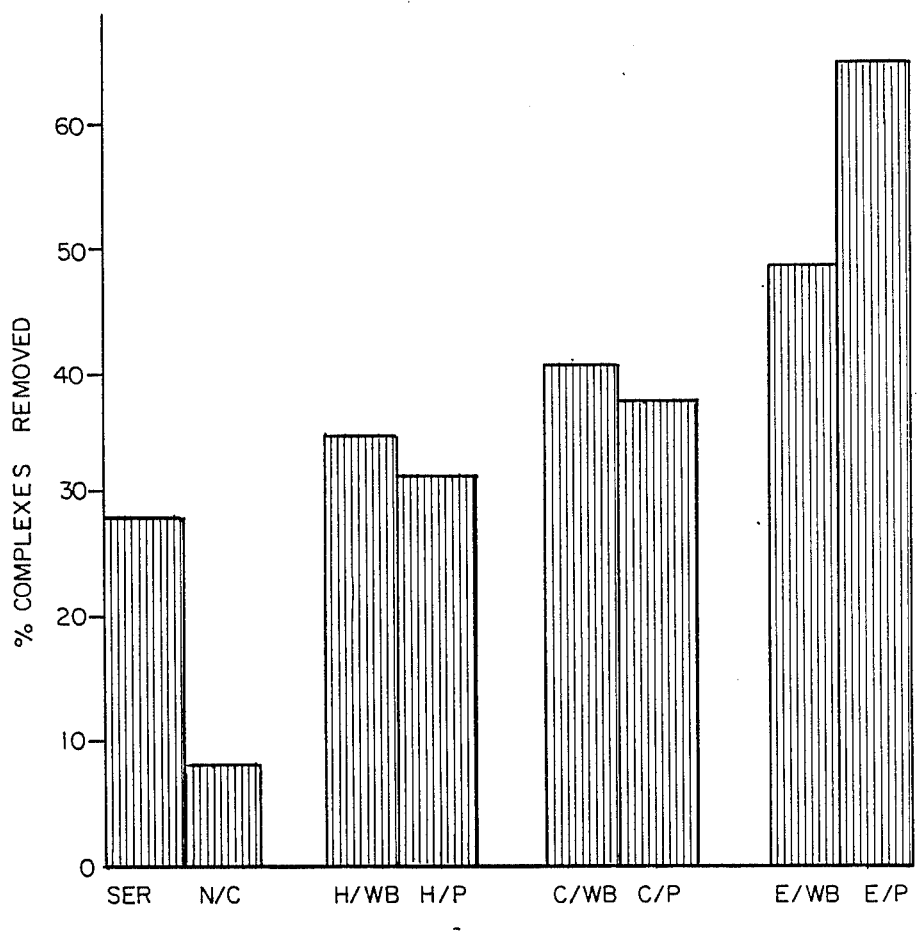
FIG. 7 is a bar graph showing the relative removal of relative immune complexes according to the present invention.

The results of this procedure are presented in Table 7 and are graphically illustrated in FIG. 7.

Referring both to Table 7 and FIG. 7 it is clearly apparent that the presence of anticoagulants is without deleterious effect upon the ability of glycoprotein treated supports to remove immune complexes from either plasma or whole blood. This is expected since calcium is not required for the glycoprotein-immune complex interaction which fixes the complexes to the support as taught in the previous examples. Uncoated polystyrene support materials were unable to affix significant amounts of immune complex, again in agreement with the principles taught in Examples 1-3.

As is demonstrated by the teaching in this example, glycoprotein films applied to suitable supporting materials will be highly useful for the purpose of removing simple or extended immune complexes, including those comprising anti-antibodies like rheumatoid factor and their targets from whole blood or from plasma, regardless of the anticoagulants which may be present. This attribute makes it possible to adsorb immune complexes from the blood for therapeutic treatment of any immune-complex associated disease or disorder. It also adds to the utility of the procedure since the column can serve to concentrate anti-antibody-containing complexes such as rheumatoid factors and their targets, or certain rare antibody or antigen types present in the immune complexes. Following elution of said concentrated complexes from such columns, detection of rare antigens or antibodies can be performed with great facility using the assay method taught in Examples 1 and 5.

TABLE 7

| Column Loaded With | % Complexes Removed |
| --- | --- |
| Serum | 28% |
| Serum* | 8% |
| Heparin-treated whole blood | 34% |
| Heparin-treated plasma | 31% |
| Citrate-treated whole blood | 40% |
| Citrate-treated plasma | 37% |
| EDTA-treated whole blood | 48% |
| EDTA-treated plasma | 64% |

*Serum passaged through non-coated polystyrene columns

Legend:
Removal of Immune Complexes from Serum, Plasma, and Whole Blood using columns of Glycoprotein-coated Polystyrene Beads.

Blood was drawn into separate vacutainer brand tubes, each containing a different anticoagulant. The tubes were designated as follows:

Heparin, final blood concentration, 28 USP units/ml.

Citrate, final blood concentration of sodium citrate, 3.5 mg/ml.

EDTA, final blood concentration of sodium EDTA, 1.5 mg/ml.

After collection, an aliquot of each blood specimen was subjected to centrifugation and the plasma withdrawn. These plasma samples were used whenever indicated in the table. Whole blood refers to the anticoagulated specimen prior to centrifugation. Serum refers to a blood specimen which was drawn into a tube and allowed to clot prior to separation of the fluidic component.

For the column extraction of immune complexes, 0.25 ml aliquots of each sample noted in the table were added to each of 8 columns and allowed to incubate for 30 minutes at 37° C. The remaining serum components were eluted from the columns with 3.75 ml PBS and the eluted assayed for immune complexes. The percentage of complexes removed was calculated as noted in the accompanying text.

For the purposes of comparison, serum controls were also passed through columns prepared with thin glycoprotein films on polystyrene supports. Such serum controls were devoid of anticoagulants. The purpose of such serum controls was to demonstrate that, regardless of how high or low the anticoagulant concentration, there was no deleterious effect of said anticoagulants on the ability of glycoprotein-coated substrates to remove immune complexes from fluids for either the purposes of assay or of immune complex immunoadsorption from blood or plasma for the purpose of therapeutic apheretic applications.

For the column extraction of immune complexes, 0.25 ml aliquots of each sample noted in the table were added to each of 8 columns and allowed to incubated for 30 minutes at 37° C. The remaining serum components were eluted from the columns with 3.75 ml PBS and the eluate assayed for immune complexes. The percentage of complexes removed was calculated as noted in the accompanying text.

In FIG. 7, the specimen added to the column is indicated below the bar. The height of the bar represents the percentage of immune complexes removed from the specimen. Abbreviations used are as follows:
SER: Serum
N/C: Serum passaged over a column of non-coated polystyrene.
H/WB: Heparin treated whole blood.
H/P: Plasma derived from heparin treated whole blood.
C/WB: Citrate treated whole blood.
C/P: Plasma derived from citrate treated whole blood.
E/WP: EDTA treated whole blood.
E/P: Plasma derived from EDTA treated whole blood.

Example 8

Films of glycosylated polypeptides are capable of affixing immune complexes comprising wide variations in molecular size and composition. To illustrate this capacity, plasma derived from an individual suffering from systemic lupus erythematosus was subjected to column chromatography over a cylindrical column of agarose A15M (BioRad) measuring 1.6×35 cm. Agarose A15M columns are molecular sieves which separate molecular speices according to size over a range of 40,000 to 15,000,000 Daltons. The column was eluted with phosphate buffered saline. Protein content of the eluate was monitored using an Isco UV monitor. The eluate was fractionated into 2.8 ml aliquots as it emerged from the column. Each fraction was assayed for immune complex content as described in Examples 1 and %. Antibody class detection (IgG-, IgM-, and IgA-containing complexes) was facilitated using peroxidase labelled antihuman IgG, IgM, or IgA as appropriate for the assay.

Figure 8:
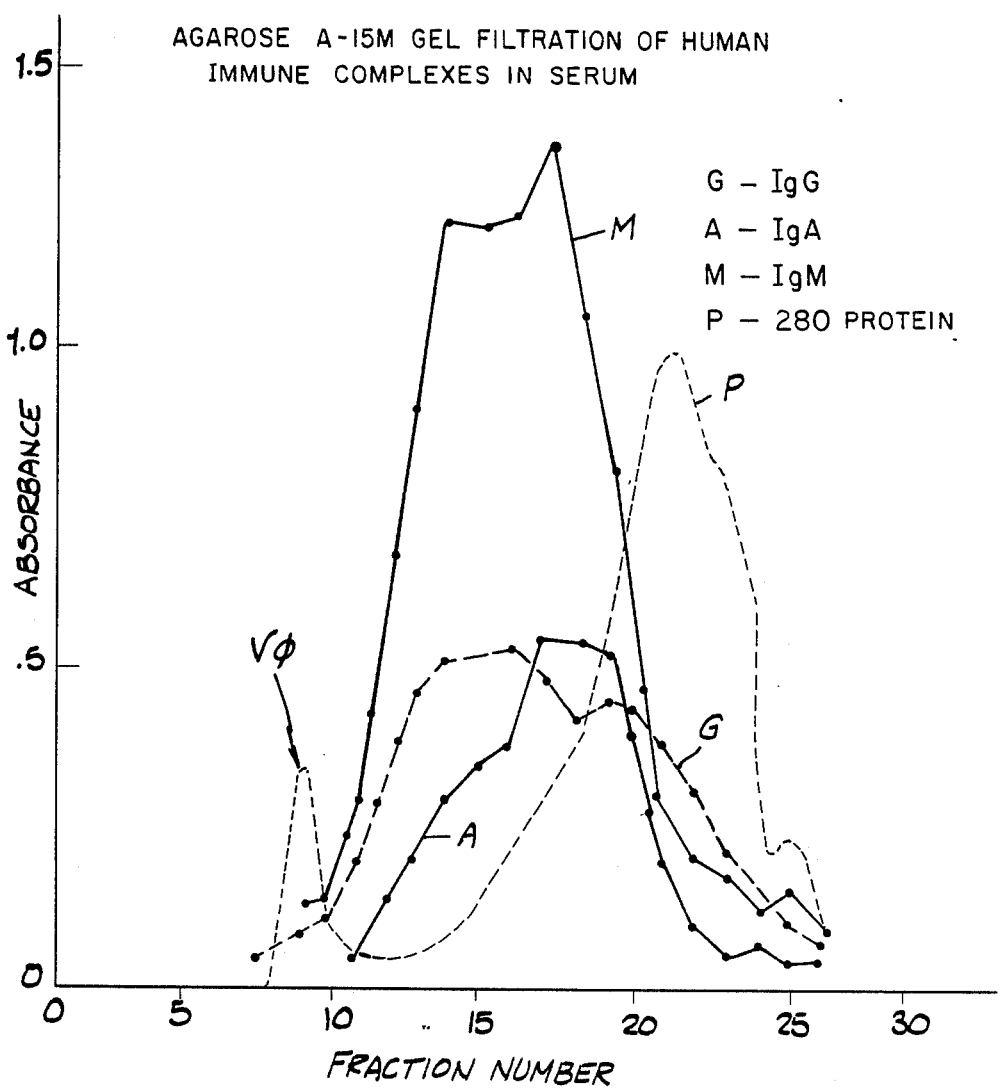
FIG. 8 is a graph showing gel filtration of human serum and resolution and detection of immune complexes therefrom.

Upon reference to FIG. 8, it is apparent that peak immune complex binding (revealed by the immune complex assay procedure) was significantly displaced from the protein peaks (revealed by the OD$_{280}$ monitor). Furthermore, complexes containing a predominant class of immunoglobulin behaved in a manner distinct from complexes containing other immunoglobulin classes. Calibration of the column (FIG. 9), revealed that the immune complexes found in this patient had molecular masses ranging from 200,000 to more than 5,000,000 Daltons. The utility of the assay procedure described in this patent can be best appreciated in light of such characterization studies. Very few assay procedures possess such wide ranges of applicability towards the measurement of simple and extended immune complexes.

Legend:
FIG. 8: Agarose A15M Gel Filtration of Human Immune Complexes in Serum

Immune complexes were separated according to size on a column of Agarose A15M measuring 1.6 cm diameter by 35 cm length. The abscissa and ordinate indicate the elution fraction number and absorbance respectively. One column volume corresponds to approximately 25 fractions. A 1.0 ml sample of human serum obtained from an individual suffering from systemic lupus erythematosus was applied to the top of the column at fraction 0. Separation and elution were performed with phosphate buffered saline described earlier (0.15M NaCl with 0.01M potassium phosphate, pH 7.4).

In FIG. 8, P represents the absorbance monitored at 280 nm with an Isco flow monitor. The void volume of the column is noted by the arrow labelled $V_0$. The absorbances resulting from immune complex assays specific for IgG, IgA, and IgM are indicated by the appropriate line (labelled G, A, or M). The absorbance for IgM-containing complexes (curve M) is the result of enhanced sensitivity of the IgM probe used for the assay. The sensitivity of G and A specific antibodies appears to be approximately equal under controlled conditions in the laboratory.

Figure 9:
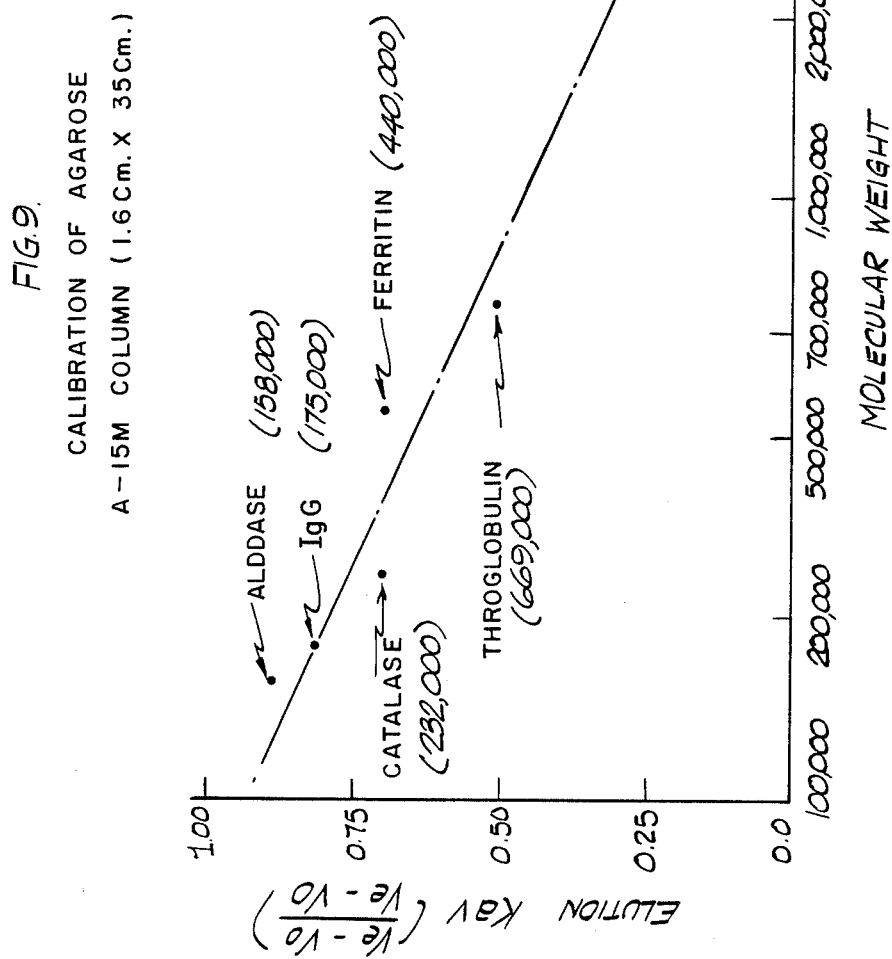
FIG. 9 is a graph showing molecular weight calibration of the gel filtration shown in FIG. 8.

Legend:
FIG. 9: Calibration of Agarose A15M Column

The chromatography column described in the Legend for FIG. 9 was calibrated using a variety of proteins to determine the molecular weight range for immune complexes detected by the immune complex assay. Five different column elutions were performed, one each with purified aldolase (m.w. 158,000), IgG (m.w. 170,000), catalase (m.w. 232,000), ferritin (m.w. 440,000), and thyroglobulin (m.w. 670,000). The void volume was determined in a sixth run using both aggregated protein (m.w. greater than 20,000) and blue dextran (m.w. range between 1,000,000 and 50,000,000). The column volume was determined by chromatography of ribonuclease (m.w. 13,000). The elution $K_{av}$ depicted on the ordinate was calculated by the following formula:

$$K_{av} = \frac{(V_e - V_0)}{(V_c - V_0)}$$

Where:
$K_{av}$ = Partition Coefficient
$V_e$ = Elution Volume
$V_0$ = Void Volume
$V_c$ = Column Volume The log of the molecular weight is plotted on the abscissa of FIG. 9. The resulting line was extrapolated to the Y intercept, yielding an exclusion limit of 10,000,000 Daltons. Molecular weights for protein fractions subject to chromatography on this medium may be determined by first calculating the $K_{av}$, then referring to FIG. 9 for the molecular mass.

EXAMPLE 9

The purpose of this example is to further illustrate the utility of the assay procedure for immune complexes as described heretofore. Many autoimmune disorders such as systemic lupus erythematosus are difficult for the physician to diagnose in the early stages, yet yield complexes comprising an antigen or a small family of antigens. If these immune complexes could be tested for their antigenic components, it would greatly facilitate disease recognition and diagnosis.

If one contacts the coated plates described in Example 1 with blood serum or plasma or whole blood then the immune complexes, including the antigenic components and expose "Fab" binding sites thereof, will adhere to the coating, thus to the solid support. The addition of either enzyme-labelled antibodies specific for the antigen or family of antigens unique for the given autoimmune disease, or enzyme-labelled antigens as may be found in the complex, which can bind to exposed "Fab" portions of the immune complex, will the demonstrate the presence of the complexed, disease-specific, antigen in question through the development of the characteristic color following addition of substrate. On the other hand, should the immune complexes not contain either such antigens nor "Fab" regions as may be specific or selective for the disease, then the addition of enzyme-labelled antibodies or antigens will fail to form color after substrate addition. As a consequence, antigen specificity for immune complex testing will greatly facilitate the task of autoimmune disease diagnosis and disease progress monitoring mandatory for good medical care and practice. The utility of this procedure can readily be appreciated by one skilled in the healing arts.

EXAMPLE 10

The following demonstrates enhancement of glycoprotein coats by secondary coating with another species of glycoprotein. Some immune complexes are unable to bind directly to the glycoprotein coating described in Examples 1-9. The capacity and selectivity of the primary coating is enhanced in such instances by secondarily coating with a substance such as rheumatoid factor, anti-antibodies, or other agents possessing additional specificity for both the plate coat and immune complexes. These materials improve immune complex binding to the solid support by enhancing interactions with immune complexes at sites which are remote from the sites recognized and utilized by the primary coating reagent.

To demonstrate this effect, rabbit antibodies were used to form simple immune complexes with goat serum albumin. Such in vitro formed immune complexes do not bind well with the primary plate coating. Immunochemical quantitation of precipitation was performed by the capillary precipitin method, in which the height of the precipitate forming in a capillary tube is directly related to the quantity of precipitate present in the mixture. All quantitative precipitin tests determined the amount of insoluble immune complex, thus indicating the endpoint of soluble immune complex formation.

The presence of soluble immune complexes was determined in the following way:

1. A plate was sensitized with bovine gammaglobulin as described in Examples 1 and. The plate was then washed carefully with PBS-Tween ® to remove the unfixed glyco-protein.

2. The wells in the plate were incubated with a preparation of human rheumatoid factor diluted 1:16 for 30 minutes at 37° C.

3. Immune complexes were formed by reacting 100 microliters of purified rabbit anti-goat serum albumin with an equal volume of goat serum albumin. The ranges tested were from 7.8 to 100 ug antigen/ml. Two fold increments of antigen concentration were used for the study. Fifty microliters of the 200 microliter preparation were aspirated into capillary tubes for the capillary precipitin test. The remainder was incubated at 37° C. for 30 minutes, cleared on insoluble immune complexes by centrifugation and used for assay without further dilution.

4. One hundred microliters of immune complex-containing aliquot (step 3) were contacted with the appropriately labelled wells of the plate prepared in steps 1 and 2 above. The plate and its contents were incubated at 37° C. for 1 hour. Following incubation, the plate was washed free of unbound material as described in Examples 1 and 2.

5. The presence of immune complexes was demonstrated by incubating the plate with horseradish peroxidase labelled anti-rabbit antibodies as described for the determination of human immune complexes in Examples 1 and 2. Peroxidase activity in the washed plates was determined by the oxidation of orthophenylenediamine as described in Example 1. The results of this study are listed in Table 8 below and depicted in FIG. 10.

TABLE 8
SOLUBLE IMMUNE COMPLEX ASSAY USING AUGMENTED PLATES

| Antigen Concentration | Precipitate Height (mm) | Immune Complex Assay (OD) |
|---|---|---|
| 1000.0 | 0.0 | 0.995 |
| 500.0 | 0.0 | 1.687 |
| 250.0 | 0.0 | 2.200 |
| 125.0 | 0.5 | 0.126 |
| 62.5 | 4.5 | 0.080 |
| 31.3 | 3.5 | 0.095 |
| 15.6 | 1.5 | 0.094 |
| 7.8 | 0.2 | 0.190 |

Legend:

One hundred microliter aliquots of goat serum albumin (antigen) were reacted with an equal volume of rabbit anti-goat albumin at 37° for 30 minutes. The antigen concentrations are listed under the heading. After incubation, the insoluble immune complexes were estimated by the capillary precipitation test. These results are shown under the "Precipitate Height" heading. The augmented immune complex test, adapted for rabbit IgG as described in Example 10, was used to detect soluble immune complexes. The absorbances resulting from the assay of each supernatant fraction are listed under the "Immune Complex Assay OD" heading.

Figure 10:
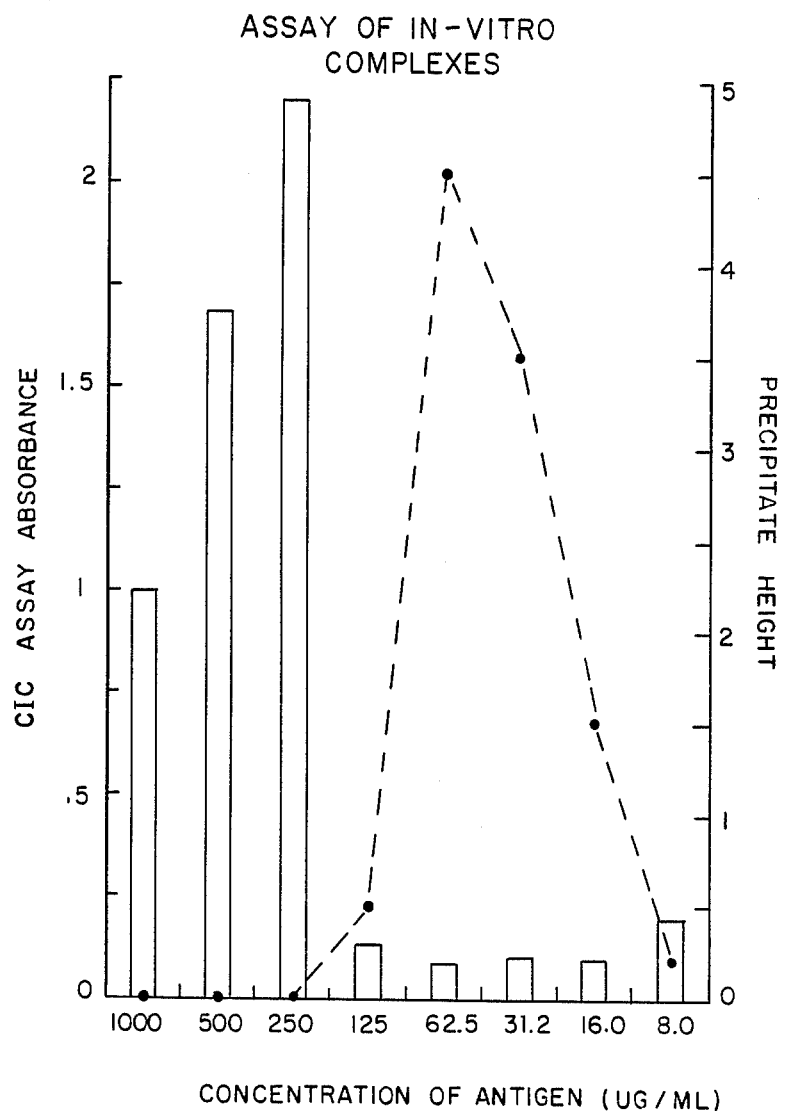
FIG. 10 is a graph showing the ability of composite coated substrates to take up soluble complexes.

The abscissa of FIG. 10 representing the concentration of goat serum albumin (ug/ml) (antigen) used in the reaction tubes. The left ordinate represents the absorbance found after conducting the augmented assay for soluble immune complexes described in Example 10, i.e., the amount of soluble immune complex found in the reaction supernatant. The right ordinate represents the height of the precipitate column measured in the capillary precipitin test for insoluble immune complexes.

Bar height in FIG. 10 represents the absorbance found in the soluble immune complex assay, while the closed circles represent the precipitate height in the capillary precipitin test.

The bovine gammaglobulin-rheumatoid factor composite coating markedly enhanced the uptake or binding of soluble immune complexes composed of rabbit antibodies and goat serum albumin. The maximum quantity of soluble immune complexes detected by the assay in antigen excess preceded the maximum quantity of insoluble immune complexes determined by the capillary precipitin method. Immune complexes were not detected at or around equivalence by the soluble assay procedure because the complexes were quantitatively removed by precipitation. This conclusion was verified by performing a similar C1q test on the same starting material. Soluble immune complexes were again detected at far antibody access (7.8 ug/ml). As for antigen excess, far antibody excess produces an abundance of soluble immune complexes.

The example provides an additional method whereby immune complexes may be affixed to solid supports for assay or removal from circulation. The composite medium provides an excellent method for entrapment of immune complexes regardless of their origin or composition.

The foregoing examples serve to illustrate the efficacy and utility of thin glycoprotein films to affix immune complexes to solid supports. While the illustrating examples have shown that the antibody molecules present in the complexes may readily be determined, there is no reason to limit the detection method to the antibody classes or subclasses contained therein. Further utility of the method is afforded through the use of antigen specific detection means whereby the disease state may be ascertained. The following descriptions illustrate means whereby such detection may be performed.

Antigen and antibody components in immune complexes possess unoccupied binding sites which can be detected through specific interaction with labelled or conjugated materials. As a consequence, immune complex fixation as described in Examples 1, 3 and 5 followed by incubation with an enzyme conjugated antigen will lead to subsequent fixation of the conjugated antigen. This property will lead to antigen-specific enzyme-catalyzed reaction if the antibodies directed against the antigen are present in the complex. As a consequence, the enzyme immunoassay will be positive if the complex contains antibodies directed against the antigenic substance, while the enzyme immunoassay will be negative if these components are absent. This method affords additional utility by permitting disease-specific inquiry as to the precise antibody composition of the complex. Conjugation need not be limited to enzymes. Addition of fluorescent or luminescent chemicals such as fluorescein or luciferin or the like to the antigen will impart fluorescence or luminescence to the complex if said antibody substances are present; similarly, conjugation of the antigen with a radionuclide will impart radioactivity to the complex provided said antibody substances are present in the previously affixed complex. Many other methods of detection also exist, and each of these methods will yield positive indications provided that the antibody component exists in the complex affixed according to the methods described herein.

Likewise, the presence of the precise antigens in the complex, as described herein will also permit the detection of such antigens using conjugated antibodies directed against that antigen. As a consequence, if one incubates enzyme-conjugated antibodies with an immobilized immune complex prepared according to the method described herein, the enzyme-catalyzed reaction will indicate the presence of said antigens in the complex. Conjugation again need not be limited to enzymes. Addition of fluorescent or luminescent chemicals such as fluorescein or the like to the antibody will impart fluorescence or luciferin to the complex if said antigenic substances are present. Similarly, conjugation of the antibody with a radionuclide will impart radioactivity to the complex provided said antigenic substances are present in the previously affixed complex. As with the detection of antibodies described, many other methods of detection for the antigens also exist; each of these methods will yield positive indications provided that the antigenic component exists in the complex affixed according to the methods described herein.

The described technology for providing supports with a composite layer of immunologically non-specific peptide linked amino acids including oligopeptides, modified oligopeptides, polypeptides, modified polypeptides, proteins, and modified proteins, together with anti-antibodies or rheumatoid factor to form a composite coating which has the ability to directly and selectively affix immune complexes by absorption, adsorption or other mechanisms of attachment, and has broad utility in either assaying bodily fluids for the presence of circulating immune complexes or for removing circulating immune complexes from body fluids. In particular, glycosylation of any of the foregoing immunologically non-specific peptide linked amino acid based classifications should produce the most useful compositions for isolation and identification of immune complexes. The ease of use and widespread applicability of this technology will be readily appreciated. The treatment of solid supports in the ways described affords many important and useful approaches to the detection and treatment of autoimmune diseases, suggesting a wide variety of new procedures. Such procedures can include, but are not limited to detection of the antibody class and subclass composition of the immune complex, determination of the antigen nature of the immune complex, and removal of such complexes as may be present in serum, other bodily fluid, or fluid of any source, whether corporeal or extracorporeal. The techniques described herein therefore, have widespread applicability and broad utility for directly removing circulating immune complexes from serum.

In addition, the described composite layer formation enables the design of an assay for rheumatoid factor since the glycoprotein coating bonds rheumatoid factor. A suitable probe consisting for example of denatured, tagged IgG can then be used to preferentially bond to the immobilized rheumatoid factor from the fluid sample to provide a direct reading of the of the rheumatoid factor that was present.

Without being bound to any specific theory, it is contemplated that varying degrees of glycosylation or other similar, functionally equivalent substituents to immunologically naive species of the described oligopeptides, polypeptides and proteins will produce a family of materials having the capability of directly attaching immune complexes present in the serum for the purpose of detection and removal.

It is additionally contemplated that composite capture reagents may be prepared composed of two or more glycosylated polypeptides, proteins, or similar substances which further enhance the affinity of the substrate for immune complexes, and this augmented family of materials will greatly facilitate the removal of immune complexes from fluids for assay or removal.

It is contemplated that the inventive concepts herein described may be variously otherwise embodied and it is intended that the appended claims be construed to include alternative embodiments of the invention except insofar as limited by the prior art.

We claim:

1. A method of performing an immunoassay of a body fluid specimen to determine the composition and/or concentration of immune complexes present in said specimen, comprising the steps of:

introducing the specimen to be assayed and a combination of immunologically non-specific alkaline treated gammaglobulin derived from animals not immunized against any antigenic determinant and an additional fixative agent selected from the group consisting of anti-antibodies or rheumatoid factors or combinations thereof onto a receiving means, said combination being selected so as to be capable of adhering to said receiving means and having the capability of binding to the immune complexes which may be present in said specimen;

permitting said combination to bind immune complexes present in said specimen; and treating said affixed immune complexes in a preselected manner to produce an indication of the composition and/or concentration of the immune complexes and the antibody and antigen components present in said specimen.

2. The method according to claim 1, including the steps of treating said receiving means with said combination in a manner to form a composite layer of said combination on said receiving means, said receiving means comprising a solid phase base capable of receiving a specimen to be assayed, and thereafter contacting said specimen to be assayed with said composite containing receiving means.

3. A method for removing immune complexes from body fluids comprising the steps of:

(1) fixing a composition containing immunologically non-specific alkaline treated gammaglobulin derived from animals not immunized against any antigenic determinant and a bonding agent selected from the group consisting of anti-antibodies or rheumatoid factor, to a substrate under conditions preselected to facilitate the fixation of such composition to said substrate to form a composite coating thereon;

(2) contacting said composite coating with specific body fluids in a manner to facilitate adherence of any immune complexes contained in the bodily fluid to said coating;

whereby immune complexes present in said bodily fluid are fixed to said coating on said substrate.

4. A method of removing immune complexes from bodily fluid characterized by the steps of:

(1) fixing a composite composition containing an immunologically non-specific alkaline treated gammaglobulin derived from animals not immunized against any antigenic determinant in combination with an anti-antibody or rheumatoid factor or combination thereof to a substrate;

(2) contacting said fixed composite coating on said substrate with a solution containing immune complexes and phosphate buffered saline; and (3) promoting adherence of immune complexes contained in the solution to said composite coating by incubation at a preselected temperature and for a sufficient period of time to adhere immune complexes to said composite coating.

5. An article for selectively removing immune complexes from body fluids placed in contact with such article, comprising:

support means adapted to be contracted with solutions containing immune complexes; and coating means comprising a composite composition containing immunologically non-specific alkaline treated gammaglobulin derived from animals not immunized against any antigenic determinant affixed to said support means in combination with a bonding agent selected from the group consisting of anti-antibodies or rheumatoid factor or combinations thereof, such coating being capable of adhering immune complexes present in specific body fluids when such body fluids are placed in contact with said coating;

whereby immune complexes present in such body fluids may be selectively attached to said coating.

6. A method of producing an article having the capability of directly and selectively affixing immune complexes to such prepared substrate, characterized by the steps of:

providing a substrate having a receiving surface;

contacting said substrate with a composition comprising an alkaline treated gammaglobulin derived from animals not immunized against any antigenic determinant in combination with other proteins, anti-antibodies or rheumatoid factor or combinations thereof, which are capable of being attached to said composition to form a composite coating and which is capable of adhering immune complexes present in fluids that are placed in contact with said coating in a manner that permits subsequent identification of the presence of immune complexes in said fluid.

7. A method for performing an immunoassay of a body fluid specimen to determine the composition and/or concentration of rheumatoid factor present in said specimen, comprising the steps of:

forming a coating on a substrate, said coating consisting essentially of an immunologically non-specific alkaline treated gammaglobulin derived from animals not immunized against any antigenic determinant;

contacting said coating with a specimen of body fluid diluted with an immunologically non-specific alkaline treated gammaglobulin derived from animals not immunized against any antigenic determinant;

permitting the rheumatoid factor present in said specimen to bind said coating; and treating said affixed rheumatoid factor in a preselected manner to produce an indication of the concentration of the rheumatoid factor present in said specimen.

* * * * *